United States Patent [19]

Kartenbeck

[11] Patent Number: 4,552,640

[45] Date of Patent: Nov. 12, 1985

[54] ELECTROPHORETIC APPARATUS FOR THE QUANTITATIVE ELUTION OF PROTEINS OR POLYPEPTIDES FROM A GEL

[75] Inventor: Jürgen Kartenbeck, Heidelberg, Fed. Rep. of Germany

[73] Assignee: Deutsches Krebsforschungszentrum Stiftung Des Offentichen Rechts, Fed. Rep. of Germany

[21] Appl. No.: 442,735

[22] Filed: Nov. 18, 1982

[30] Foreign Application Priority Data

Dec. 2, 1981 [DE] Fed. Rep. of Germany ....... 3147611

[51] Int. Cl.[4] ............................................. G01N 27/28
[52] U.S. Cl. ................................. 204/301; 204/299 R
[58] Field of Search ............... 204/180 R, 299 R, 301, 204/180 G

[56] References Cited

U.S. PATENT DOCUMENTS

| | | | |
|---|---|---|---|
| 3,533,933 | 10/1970 | Strauch | 204/180 G |
| 3,579,433 | 5/1971 | Dahlgren | 204/299 R |
| 3,773,648 | 11/1973 | Van Welzen et al. | 204/299 R |
| 3,980,546 | 9/1976 | Caccavo | 204/299 R |

OTHER PUBLICATIONS

Laemmli, Nature, vol. 227, "Cleavage of Structural Proteins During the Assembly of the Head of Bacteriophage T4", pp. 680-685, 1970.

Jean O. Thomas et al, Proc. Nat. Acad. Sci. USA, vol. 72, No. 7, "An Octamer of Histones in Chromatin and Free in Solution", pp. 2626-2630, 1975.

*Primary Examiner*—Andrew H. Metz
*Assistant Examiner*—B. J. Boggs, Jr.
*Attorney, Agent, or Firm*—Sughrue, Mion, Zinn, Macpeak and Seas

[57] ABSTRACT

An apparatus for the quantitative elution of proteins or polypeptides from a gel by means of electrophoresis. The apparatus includes an upper chamber for holding a buffer solution containing the gel from which the proteins or polypeptides are to be eluted. An upper electrode is provided in the upper chamber. A lower chamber for holding a buffer solution is disposed beneath the upper chamber and includes a lower electrode. A septum separates the upper chamber from the lower chamber. A connecting passage in the septum connects the upper and lower chambers. A collecting capsule for the proteins or polypeptides is disposed at the end of the connecting passage in the lower chamber, and is adapted to be suspended in the buffer solution which is to be held in the lower chamber.

8 Claims, 1 Drawing Figure

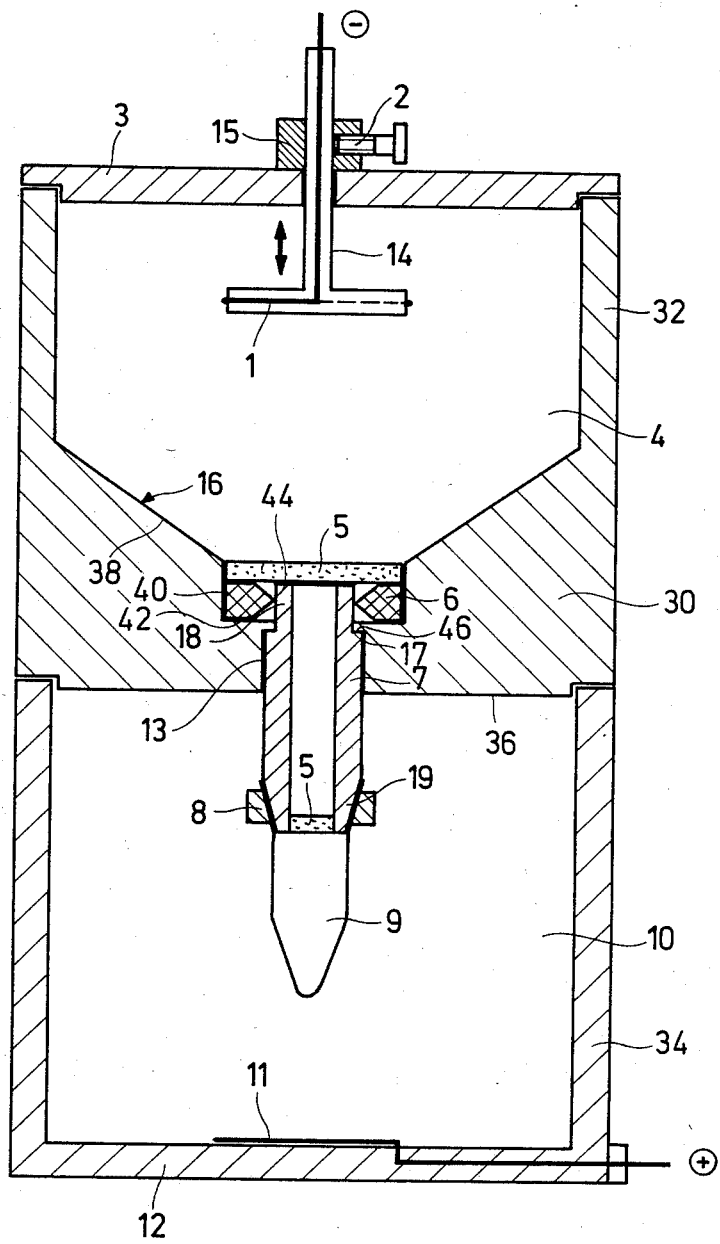

ELECTROPHORETIC APPARATUS FOR THE QUANTITATIVE ELUTION OF PROTEINS OR POLYPEPTIDES FROM A GEL

BACKGROUND OF THE INVENTION

The present invention relates to an apparatus for the quantitative elution of proteins or polypeptides from a gel by means of elctrophoresis.

Protein mixtures, such as viruses, and isolated biological membranes, etc. (separated according to SDS (sodium dodecyl sulfate)/polyacrylamide gel electrophoresis (see e.g. Laemmli, Nature Vol. 227, pp. 680 to 685, 1970; and Thomas and Kornberg, Proc. Nat. Acad. Sci. U.S.A. Vol. 72, pp. 2226 to 2630, 1975) are represented as individual bands in a plate gel. These bands correspond to individual proteins having the corresponding molecular weight. In order to utilize the thus separated proteins, or polypeptides, for other purposes, the bands are separated from the plate gel and collected. The protein retained in the network of the polyacrylamide is electrophoretically eluted. Generally a running buffer such as 5 mM tris-glycin, pH 8.6 0,2% SDS and 0.5% mercaptoethanol is used as the elution buffer.

SUMMARY OF THE INVENTION

It is an object of the present invention to provide an apparatus with which isolation of even larger quantities of electrophoretically separated proteins or polypeptides is possible in a desired concentration.

The above and other objects are accomplished in accordance with the invention wherein an apparatus is provided for the quantitative elution of proteins or polypeptides from a gel by means of electrophoresis. The apparatus includes an upper electrode chamber for holding a buffer solution containing the gel from which the proteins or polypeptides are to be eluted. An upper electrode is mounted in the upper electrode chamber. A lower electrode chamber for holding buffer solution is disposed beneath the upper electrode chamber. A lower electrode is mounted in the lower electrode chamber. A septum separates the upper electrode chamber from the lower electrode chamber. The septum is provided with a connecting passage for connecting the upper and lower chambers. A collecting capsule for collecting the proteins or polypeptides is disposed at the end of the connecting passage in the lower electrode chamber, and is adapted to be suspended in the buffer solution which is to be held in the lower chamber.

In operating the apparatus, the application of a voltage potential between the upper and lower electrodes causes the proteins or polypeptides to be eluted from the gel in the upper chamber and collected in the collecting capsule.

It is to be understood that both the foregoing general description and the following detailed description are exemplary, but are not restrictive of the invention.

BRIEF DESCRIPTION OF THE DRAWING

The sole FIGURE is a cross-sectional view of an elution apparatus according to the invention.

DESCRIPTION OF THE PREFERRED EMBODIMENT

Referring now to the drawing, there is shown an elution apparatus which includes an upper electrode chamber 4 which is to contain a buffer solution and a lower electrode chamber 10 which is to contain the same buffer solution. The individual proteins or polypeptides separated and collected from the plate gel which are to be eluted, are placed in the buffer solution in upper electrode chamber 4.

Chambers 4 and 10, both of which can be of cylindrical design, are placed one on top of the other and are separated from each other by a septum 30. Septum 30 is provided with a connecting passage 13 which connects upper electrode chamber 4 with lower electrode chamber 10.

Chamber 4 is formed by a side wall 32, a bottom 16 and a removable top 3. Bottom 16 generally comprises the upper surface of septum 30 which preferably is integral (in one piece) with side wall 32. A negative electrode 1 is provided in top 3.

Chamber 10 is formed by a side wall 34, a bottom 12 and a top 36 which is the lower surface of septum 30. A positive electrode 11 is provided in bottom 12 of chamber 10.

Electrodes 1 and 11 are illustrated with a planar shape, but could have an annular or other suitable shape. Both electrodes 1 and 11 are disposed perpendicular to the longitudinal axis (axis of rotation) of chambers 4 and 10, which also passes through connecting passage 13.

Upper electrode 1 is fastened to a mount 14 which passes through top 3. A guide ring 15 is attached to the upper surface of top 3 and is provided with a thumb screw 2. Mount 14 passes through guide ring 15 and can be set at any desired height by adjusting thumb screw 2. Thus, upper electrode 1 can be adjusted in height with respect to the surface (not shown) of the gel-buffer solution disposed in upper electrode chamber 4. The height at which electrode 1 is set depends on the fill level of the gel-buffer solution in chamber 1 and the electrical voltage between electrodes 1 and 11. The level of the elution buffer in the upper electrode chamber 4 should be 1.5 to 2 cm below the upper rim of the chamber. The electrode 1 of the upper chamber should dipp about 1 cm into the buffer solution. The lower electrode chamber 10 should be filled with buffer up to the level of the counter ring 8.

The electrical voltage between the electrodes 1 and 11 should not exceed 100 V.

Bottom 16 of upper electrode chamber 4 is preferably constructed in the form of a funnel having a downwardly narrowing conical inclined surface 38, a funnel neck 40 which meets with inclined surface 38, and a seat 42 which meets with funnel neck 40. The lowest point of bottom 16 is at seat 42 and is joined to connecting passage 13. A small tube 7 having an upper end 44 and a lower end 19 is disposed in passage 13 and extends into the area defined by funnel neck 40 and seat 42. Tube 7 is provided with an abutment 17 which meets a corresponding abutment 46 in passage 13. Abutments 17 and 46 together define the extent to which tube 7 can be inserted from lower electrode chamber 10 into connecting passage 13 and the area defined by neck 40 and seat 42. A radial packing ring 6 is provided at neck 40 and seals tube 7 relative to upper electrode chamber 4. Sinter plates 5 may cover upper end 44 and lower end 19 of tube 7. The radial packing ring 6 is a oil seal or rubber O-ring. Glass sinter plates 5 of 150 $\mu$m to 50 $\mu$m pore sizes can be used.

Lower end 19 of tube 7 has a frustoconical shape. A dialysis capsule 9 is clamped onto end 19 by a counter cone ring 8.

In operation, the buffer solution in lower chamber 10 surrounds dialysis capsule 9. Dialysis capsule 9 is preferably a collodion sleeve with a reject limit of 10,000 Dalton, such as the SM 13200 sleeve made by Sartorius. (Sartorius GmbH, Göttingen, F.R.G.).

Proteins or polypeptides from the gel-buffer solution in upper electrode chamber 4 are eluted and collected in dialysis capsule 9 when a voltage of, for example, 80 to 100 V and a current intensity of, for example, 10 mA are applied to electrodes 1 and 11. The elution process is generally continued for 10 to 24 hours.

With a longer dialysis capsule 9, the height of lower electrode chamber 10 can be varied, for example, by means of a cylindrical intermediate piece (not shown) which can be placed on top of side wall 34.

In a further modification of the present invention, the bottom surface of upper chamber 4 can be provided with a plurality of funnel shaped portions, a corresponding number of connecting passages can be provided in septum 30, and a corresponding number of dialysis capsules can be arranged in lower electrode chamber 10 at the end of the respective passages, in order to simultaneously elute proteins in the same process step.

The top, bottom and side walls of the electrode chambers, as well as tube 13 and ring 8 are preferably made of an insulating material such as Plexiglass. The elution buffer in both chambers (4, 10) e.g. is 25 mM Tris buffer, adjusted to pH 8.6 with glycin to which 0.2% SDS and 0.5% mercaptoethanol is added.

It will be understood that the above description of the present invention is susceptible to various modifications, changes and adaptions, and the same are intended to be comprehended within the meaning and range of equivalents of the appended claims.

What is claimed is:

1. An apparatus for the quantitative elution of proteins or polypeptides from a gel by means of electrophoresis, said apparatus comprising:

an upper electrode chamber for holding a buffer solution containing the gel from which the proteins or polypeptides are to be eluted, an upper electrode in the upper electrode chamber;

a lower electrode chamber for holding a buffer solution and disposed beneath said upper electrode chamber, a lower electrode in the lower electrode chamber;

a septum separating the upper chamber from the lower chamber;

a connecting passage in the septum for connecting said upper and lower electrode chambers; and a collecting capsule for collecting the proteins of polypeptides, the collecting capsule being disposed at the end of said connecting passage in said lower electrode chamber, and adapted to be suspended in the buffer solution which is to be held in said lower electrode chamber.

2. An apparatus as defined in claim 1, wherein said upper and lower electrodes are oriented perpendicularly to a longitudinal axis passing through said connecting passage.

3. An apparatus as defined in claim 1, wherein said upper and lower electrodes have a planar shape.

4. An apparatus as defined in claim 1, wherein said upper and lower electrodes have an annular shape.

5. An apparatus as defined in claim 1, further comprising a mounting means for adjustably mounting said upper electrode in the upper electrode chamber and for coupling a supply voltage to said upper electrode.

6. An apparatus as defined in claim 1, wherein said upper electrode chamber has a bottom shaped in the form of a funnel; and further comprising a tube disposed in said connecting passage, with the passage extending from the lowest portion of the funnel shaped bottom of said upper electrode chamber to said lower electrode chamber.

7. An apparatus as defined in claim 6, further comprising a means for sealing said tube with respect to said upper electrode chamber.

8. An apparatus as defined in claim 6, wherein the tube has an end extending into said lower electrode chamber, said end has a frustoconical shape, and said collecting capsule is a dialysis capsule; and said apparatus further comprises a clamping ring for clamping said dialysis capsule onto said frustonically shaped end.

* * * * *